United States Patent [19]
McKendree

[11] Patent Number: 6,054,300
[45] Date of Patent: Apr. 25, 2000

[54] SINGLE-SITE AMPLIFICATION (SSA): METHOD FOR ACCELERATED DEVELOPMENT OF NUCLEIC ACID MARKERS

[75] Inventor: William L. McKendree, Casselberry, Fla.

[73] Assignee: The United States of America as represented by the Secretary of Agiculture, Washington, D.C.

[21] Appl. No.: 08/915,609

[22] Filed: Aug. 21, 1997

[51] Int. Cl.[7] ............... C12P 19/34; C12Q 1/68; C07H 19/00; C07H 21/04
[52] U.S. Cl. ............ 435/91.1; 435/6; 435/91.2; 536/22.1; 536/23.1; 536/24.3; 536/24.31; 536/24.32; 536/24.33; 536/25.3
[58] Field of Search ............... 435/6, 91.1, 91.2; 536/22.1, 23.1, 24.3, 24.31, 24.32, 24.33, 25.3

[56] References Cited

U.S. PATENT DOCUMENTS

| | | | |
|---|---|---|---|
| 5,210,036 | 5/1993 | Comb et al. | 435/194 |
| 5,270,184 | 12/1993 | Walker et al. | 435/91.2 |
| 5,322,785 | 6/1994 | Comb et al. | 435/194 |
| 5,352,778 | 10/1994 | Comb et al. | 536/23.2 |
| 5,411,875 | 5/1995 | Jones | 435/91.2 |
| 5,422,252 | 6/1995 | Walker et al. | 435/91.2 |
| 5,447,844 | 9/1995 | Bricker et al. | 435/6 |

OTHER PUBLICATIONS

Baker et al., *Molecular Ecology*, vol. 5, pp. 671–685 (1996).
Edwards et al., *BioTechniques*, vol. 20, pp. 758–760 (1996).
Vos et al., *Nucleic Acids Research*, vol. 23(21), pp. 4407–4414 (1995).
Tautz et al., *Nucleic Acids Research*, vol. 12(10), pp. 4127–4138 (1984).
Rico et al., *Molecular Ecology*, vol. 3, pp. 181–182 (1994).
Ostrander et al., *Proc. Natl. Acad. Sci. USA*, vol. 89, pp. 3419–3423 (1992).
Gupta et al., *Theor. Appl. Genet.*, vol. 89, pp. 998–1006 (1994).

*Primary Examiner*—Jezia Riley
*Attorney, Agent, or Firm*—M. Howard Silverstein; John D. Fado; Gail E. Poulos

[57] ABSTRACT

The present invention relates to method for isolation of DNA sequences having a target DNA of known sequence which accelerates and simplifies obtaining DNA especially from small amounts of tissue. This method uses polymerase having strand displacement capability, one primer and a circular DNA template.

4 Claims, 4 Drawing Sheets

SINGLE-SITE AMPLIFICATION (SSA): METHOD FOR ACCELERATED DEVELOPMENT OF NUCLEIC ACID MARKERS

CROSS-REFERENCE TO PROVISIONAL APPLICATION

This application claims benefit of provisional application Ser. No. 60/028,75, filed Aug. 23, 1996, now abandoned.

BACKGROUND OF THE INVENTION

1. Field of the Invention

The present invention relates to a method for obtaining a targeted DNA sequence. The sequence can be an entire coding region of a gene. The sequence can also be a template for PCR amplification. The present invention further relates to DNA sequences generated by the method.

2. Description of the Related Art

Isolation of DNA, including genes, may be performed by either classical or molecular genetic approaches. Classical methods are inherently slow and lack the specificity required to identify very small (short) regions of DNA. Molecular approaches for identifying and obtaining a target DNA sequence of interest requires (1) a synthetic DNA primer set designed to recognize the 3' and 5' ends of the target DNA element and subsequent polymerase chain reaction (PCR) amplification or (2) a nucleic acid probe that is complementary to the target DNA for hybridization.

An example of target DNA that is required for biological analysis or procedure is a molecular marker. Molecular markers are associated with any measurable phenotypic or genotypic characteristic. Markers can be used as a source of genetic "fingerprints" and as selectable markers linked to phenotypic traits of interest. Conventional markers used in plant breeding and identification include RFLPS, RAPDs and AFLP.

RFLP analysis is a hybrid of classical and molecular methodology requiring crosses between parents and analysis of parents and siblings for inheritance of a particular nucleic acid element (marker). RAPD and AFLP methods rely upon the presence within genomic DNA of target elements that will be recognized by a selected primer or primer set. These methods are limited by the relatively infrequent positioning of two target elements within a distance that allows amplification of a product of a size that will be useful for analysis by electrophoresis. Restriction fragments used in restriction length polymorphism assays (RFLP) are one example of a molecular marker. RFLP is used, for example, in breeding programs for corn, barley, Brassica (vegetable and oilseed), etc. RFLP markers are of limited utility in crops such as soybean, tomato and wheat where the number of polymorphic RFLP markers are quite small.

Simple Sequence Repeats (SSRs) are another type of marker which are more polymorphic than RFLP markers for a number of plants. SSRs, also called microsatellites, are short segments of DNA consisting of repeated short nucleotide sequences, such as for example, the DNA sequence ATATATAT which is a dinucleotide (AT) repeat with four repeats. The number of nucleotides that repeat generally varies from one to five bases; the number of repeated sequences can range from two to about forty. There are large numbers of repeats that can exist in a genome and the high level of polymorphism that may be associated with repeated sequences make SSRs valuable as molecular markers. The utility of a particular marker is determined by the number of markers available and the polymorphism of those markers. SSRs are found to be both more abundant and more polymorphic than other types of DNA markers. SSRs were first recognized and used by scientists working in human genetics. Most recently, they have been used to develop genome maps of certain animal and plant species. Scientists researching mammalian systems have produced SSR maps of the mouse and bovine genomes and learned that SSRs were well distributed along the chromosomes which is another important criteria for the utility of a molecular marker.

In plants, the use of SSRs can reveal differences among soybean varieties that are indistinguishable using standard RFLP techniques. In certain instances, SSR technology can provide additional markers that can be useful in combination with RFLP procedures. The availability of additional markers increases the probability of finding one or more markers that are tightly linked to a gene or groups of genes controlling a trait of interest. This increased probability can make marker-assisted selection even more efficient.

Conventional SSR development overcomes the limitations of the above mentioned technologies by isolation of marker elements by screening genomic DNA libraries for markers of interest. Using DNA sequence flanking the newly isolated marker (thus obtaining an "allele" for the particular SSR) synthetic oligonucleotide primers are then designed for subsequent PCR analysis of the length of the repeat element at that allele. SSR length varies considerably within alleles and SSR alleles are abundant and ubiquitous throughout the genome of most eukaryotic organisms. However, genomic library preparation requires relatively large amounts of genomic DNA, compared to RAPD or AFLP markers, and is difficult and time consuming. Library screening is also difficult and time consuming, with library preparation and screening requiring several months to complete.

Inverse PCR (Ochman et al., Genetics, Volume 120, 621–623, 1988; Triglia et al., Nucleic Acid Research, Volume 16, 8186, 1988; Silver et al., J. Virol., Volume 63, 1924–1928, 1989) permits amplification of DNA flanking a known sequence by circulization of restriction enzyme digested DNA. This permits amplification of the flanking sequence by positioning two primers, each of which binds to the known sequence "inside out" on the circle. This strategy maintains specificity at each primer binding site. However, difficulties with inverse PCR include the requirement of two restriction sites that flank the priming region and inefficient PCR amplification of closed circular DNA.

Yield is improved in conventional PCR when circular DNA template is linearized. If a restriction site is not present to linearize the circle between the 5' ends of the amplifying primers, the standard PCR amplification is less efficient than reverse PCR. Without linearization, double-stranded circular DNA is amplified much less efficiently than linear DNA (Jones et al., Biotechniques, Volume 10, 62–66, 1991). Nicking the circles, by heating, ameliorates the difficulty in amplifying closed circular double-stranded DNA, but only a small percentage of the circles are nicked between the two 5' ends of the amplifying primers. Any increase in the initial amplification efficiency is suboptimal.

U.S. Pat. No. 5,411,875 (Jones) discloses a PCR method where a single strand oligonucleotide is ligated to restriction enzyme digested DNA. The oligonucleotide is constructed to be complementary to a known region of DNA upstream from the unknown region of DNA. This is then denatured and self-annealed resulting in a single stranded loop or pan portion with a double-strand of an otherwise single-stranded handle. This permits PCR amplification of the unknown DNA using thermostable DNA polymerase having single-stranded 3' exonuclease activity. This method is susceptible to nonspecific hybridization.

There is a need in the art to be able to generate target DNA in less time with greater efficiency. The present invention provides a method, different from the related art, which eliminates genomic DNA library preparation and screening which are the most time consuming steps, typically requiring no less than three months, with total time for target DNA development being between 4–6 months.

SUMMARY OF THE INVENTION

It is therefore, an object of the present invention to provide a method for obtaining a DNA sequence that comprises and flanks a single target DNA site using a single primer and a circularized DNA template.

It is another object of the present invention to provide a method for obtaining a DNA sequence which includes at least one distinct primer site at the 5' end and at least one of the same primer site further downstream.

It is a further object of the present invention to produce DNA templates for PCR amplification using a single primer, a circularized first DNA template and a polymerase with strand displacement capability.

A still further object of the present invention is to provide a method which employs a polymerase having strand displacement activity for obtaining a DNA sequence, containing the same primer sequence at both ends, from a circular template using a single primer.

Further objects and advantages of the present invention will be apparent form the following detailed description.

DETAILED DESCRIPTION OF THE INVENTION

The present invention is a novel method for obtaining a particular target DNA sequence that can be useful as a template for amplification procedures, e.g. PCR; or can be employed as molecular markers, e.g. in distinguishing between species or strains or varieties within species or identifying the presence of a condition such as a disease. This invention will allow the accelerated development of high resolution DNA markers that may be used for fingerprinting, mapping, etc., using small amounts of tissue, (less than about 1 μg). The present invention will enable an investigator with limited experience in molecular biology, to genotype varieties of species, map an allele for disease resistance or improved yield, or carry out investigations in molecular systematics in a matter of weeks.

Examples of target DNA sequences for which this method will apply include simple sequence repeats (molecular markers, described herein), footprints remaining from retroviral excision, transposable elements or any DNA element of a length that is too short to be identified and/or isolated by conventional PCR.

Typical PCR technology requires prior knowledge of both the 3' and 5' ends of the target DNA sequence selected for amplification. This information is used to design primers that will anneal to the target sequences and allow amplification of the target sequence through PCR cycling. However, sequencing information for the desired target is not always available. The method of the present invention, Single Site Amplification (SSA), allows the production of, for example, PCR template with knowledge of only one region of the target DNA sequence, the size of which is regulated only by the primer design. Single site amplification is defined for the purposes of this application as a method for the production of single stranded DNA molecule containing a target DNA element site, of a size that is too small to be amplified per se, at no less than two locations within the molecule by virtue of its synthesis from a circular DNA template which contains one or more target DNA elements using a first primer designed to anneal to the target DNA element and prime DNA synthesis and a DNA polymerase that possesses strand displacement capability. SSA products can be used as template for PCR using a second primer complementary to the first primer. Typically, for example, the primer is approximately 15–150 base pairs in length. The method of the present invention will provide a foundation for a long needed DNA marker industry standard for use in areas such as import and export regulation, variety and ecotype identification, marker development, forensic DNA fingerprinting, etc.

It is not important to the practice of this invention to know what the target sequences are or how they are identified. The method involves identifying a target DNA and designing a set of complementary primers. The primer design is such that the oligonucleotide will specifically recognize the target DNA and provide an adequate priming site for initiation of DNA synthesis by using a polymerase having strand displacement capability. Primer design may be accomplished by using primer design software such as OLIGO™ (National Biosciences, Plymouth, Minn.). Complementary sequences less than 9 bases in length can increase the chance of hybridization of the complement to genomic sequences which are less satisfactory for identification purposes. These primers can be prepared with or without restriction endonuclease recognition sites.

Figure 1A:
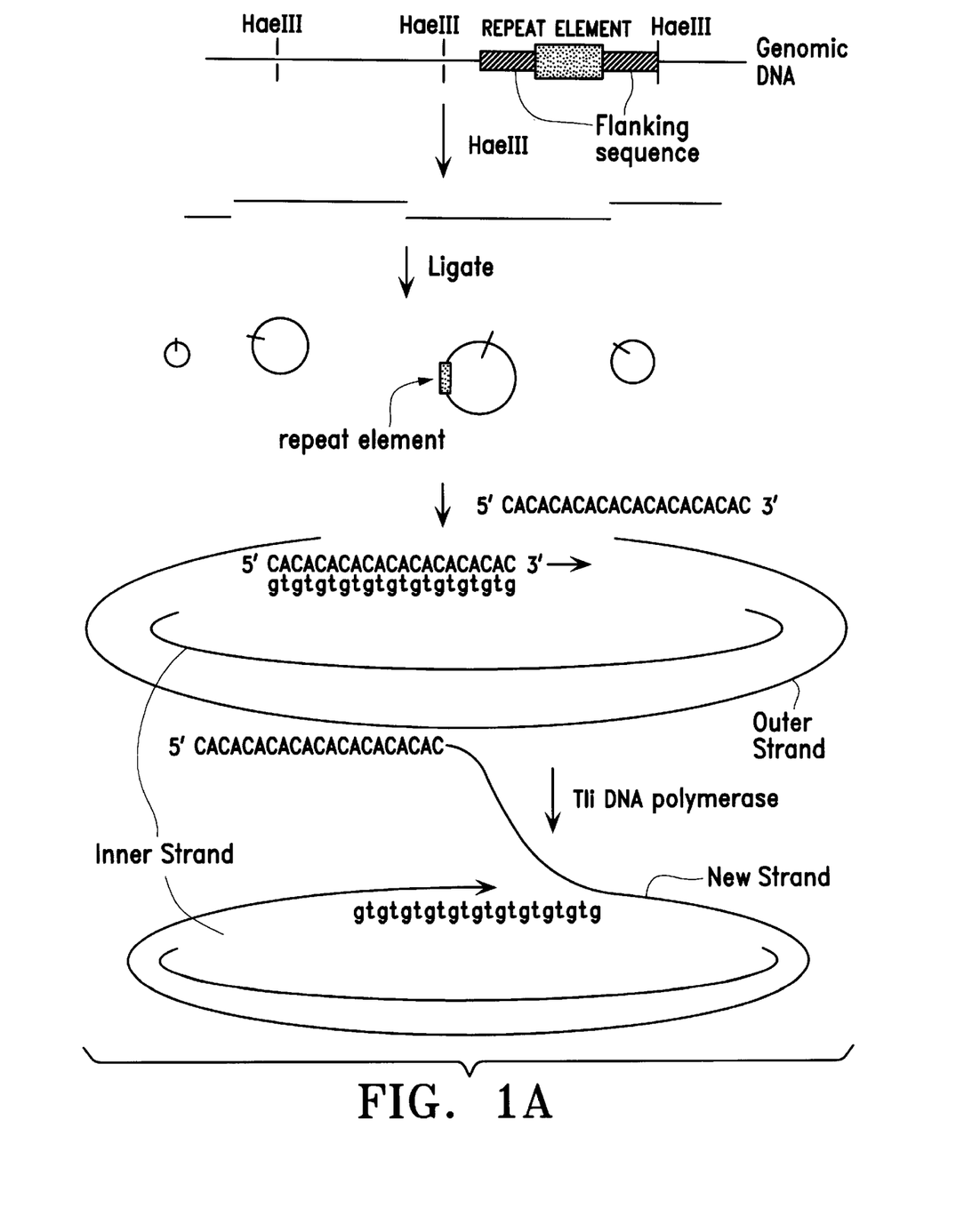
FIGS. 1A and 1B illustrate the step-wise procedure for generating multiple copies of markers according to the subject invention. In the embodiment illustrated, a microsatellite with flanking regions is generated.
Figure 1B:
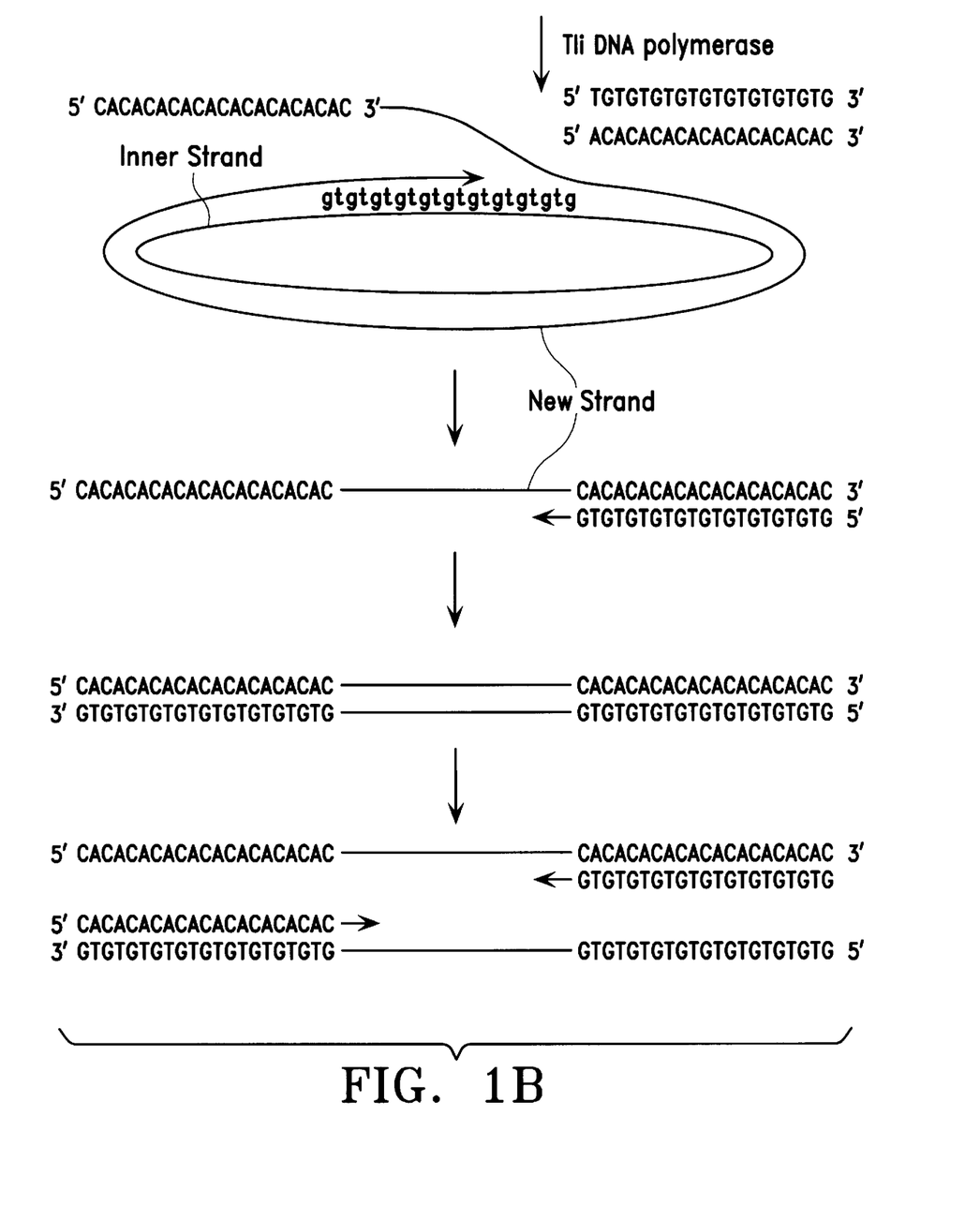

Circularized DNA template can be a plasmid, e.g., a supercoiled plasmid; relaxed, closed circular double-stranded DNA or can be obtained by treating linear genomic DNA with a restriction enzyme and then circularizing the DNA using standard techniques and procedures (Ochman et al., Genetics, Volume 120, 621–623, 1988; Triglia et al, Nucleic Acid Research, Volume 16, 8186, 1988; Silver et al., J. Virology, Volume 63, 1924–1928, 1989; all herein incorporated by reference). Examples of restriction enzymes useful in the present invention are four-base cutters such as HaeIII, Taq I, etc. The primer is annealed to the circularized DNA template and extended with DNA polymerase having strand displacement capabilities. Strand displacement capability of the polymerase allows for complete and faithful replication of the target sequence to which the primer has annealed. Examples of DNA polymerase useful in the present invention are Tli DNA polymerase (Promega Corp.) or Vent DNA polymerase (New England Biolabs; U.S. Pat. Nos. 5,210,036; 5,322,785 and 5,352,778 all three herein incorporated by reference), both are known to be thermostable, have strand displacement capability and are available commercially. Synthesis of the complementary strand continues around the circular template, displaces the primer, and proceeds beyond the point of initiation of synthesis thereby replicating the primer sequence at a second position in the polymerase product (FIGS. 1A and 1B). Single Site Amplification ends after several rounds of production of the template. To start a PCR amplification, the complement of the first primer is annealed to the extension product and the target sequence is amplified. The amplification products are then purified by size fractionation on agarose gel. The bands of interest are subcloned into a sequencing vector and the DNA sequenced to identify the target element and the flanking DNA.

The present method makes possible the production of templates that contain, for example, entire SSR alleles, enabling the generation of SSR markers within days.

The method of the present invention can also be used to generate a linear DNA molecule containing at least two target sequences from one sequence within a single-stranded DNA template, as above, and the flanking regions for these target sequences.

The method of the present invention can also be used, for example, for cloning cDNA or genomic DNA which flanks any known short target sequence. The term short is defined as having about 9–150 base pairs. The known sequence can be an SSR, or any type of dispersed repeat sequence element. Thus enabling the determination of flanking DNA sequences.

The present method can also be used to obtain entire coding regions of genes based upon a known nucleic acid sequence or by using a degenerate nucleic acid sequence derived from amino acid sequence back-translation using a polymerase having strand displacement capability which can synthesize up to 10 kb fragments. This is especially useful for obtaining plant genes which are usually less than 10 kb in length.

The following examples are presented to illustrate the use of SSA using as the target DNA an SSR marker. These examples are intended to further illustrate the invention and are not intended to limit the scope as defined by the claims.

EXAMPLE 1

SSA is demonstrated by digesting plant genomic DNA from *Arabidopsis thaliana* and *Zea maize* with either Hae III or Taq I, respectively. Approximately one μg of DNA, about 90 μl of about 10× restriction enzyme buffer which is about 25 mM Tris Acetate pH approximately 7.8, about 100 mM potassium acetate, about 10 mM magnesium acetate, and about 1 mM Dithiothreitol (Boehringer-Mannheim Biochemical), and approximately 80 μl of distilled water are combined and allowed to sit for about 2 hours on ice. Approximately 5 ml of restriction enzyme Taq I (Promega Corp.)) or Hae III (Promega Corp.)(approximately 10 U/ml) is added and allowed to react for about 2.5 hours. After the first incubation time, approximately 5 ml of enzyme is again added and allowed to react for another about 2.5 hours. Total volume is approximately 100 μl. At the end of the second incubation period. Phenol/chloroform (1:1, volume:volume) extracts are performed on the digests with about 300 ml of aqueous and about 300 ml organic. Approximately 12 μl of about 3 M NaOAc and approximately 300 μl EtOH is added to each reaction tube and DNA is precipitated from about 60 minutes to overnight at approximately 4° C. The tube is centrifuged at approximately 12,000 rpm for about 30 minutes at approximately 4° C. The pellets are washed approximately two times; once with about 70% EtOH and once with about 95% EtOH. The pellets are air dried. The dried pellets are dissolved in about 25 μl TE (about 10 mM Tris base and about 1 mM EDTA, both at about pH=8). DNA concentration was determined by measuring A260 using conversion of 1.0 Absorbance units=approximately 50 μg/ml.

Approximately 100 μg of DNA prepared above, approximately 40 μl about 10× ligation buffer (Boehringer Mannheim Biochemical), about 5 μl DNA ligase (approximately 1 unit/μl) and distilled water to bring the final volume to about 200 μl is incubated overnight at approximately 15° C. in order to ligate the DNA to form circular DNA.

Figure 2:
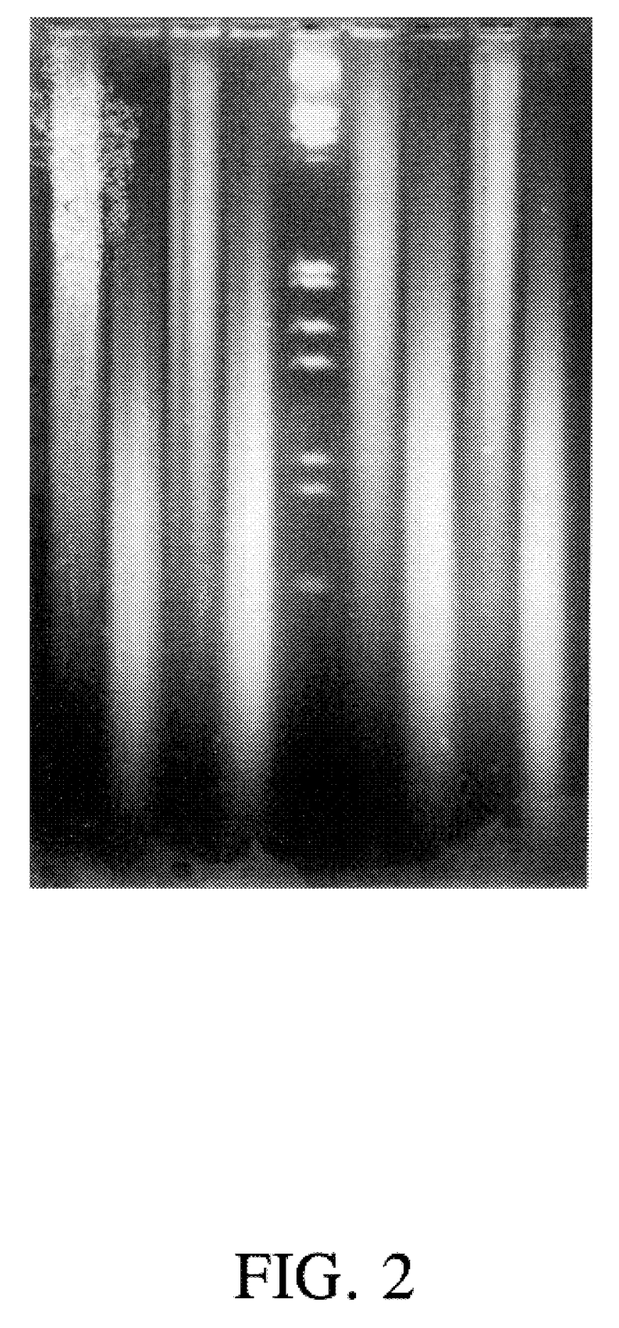
FIG. 2 shows electrophoretic separation of plant genomic DNA prepared by the method of the subject invention.
Figure 3:
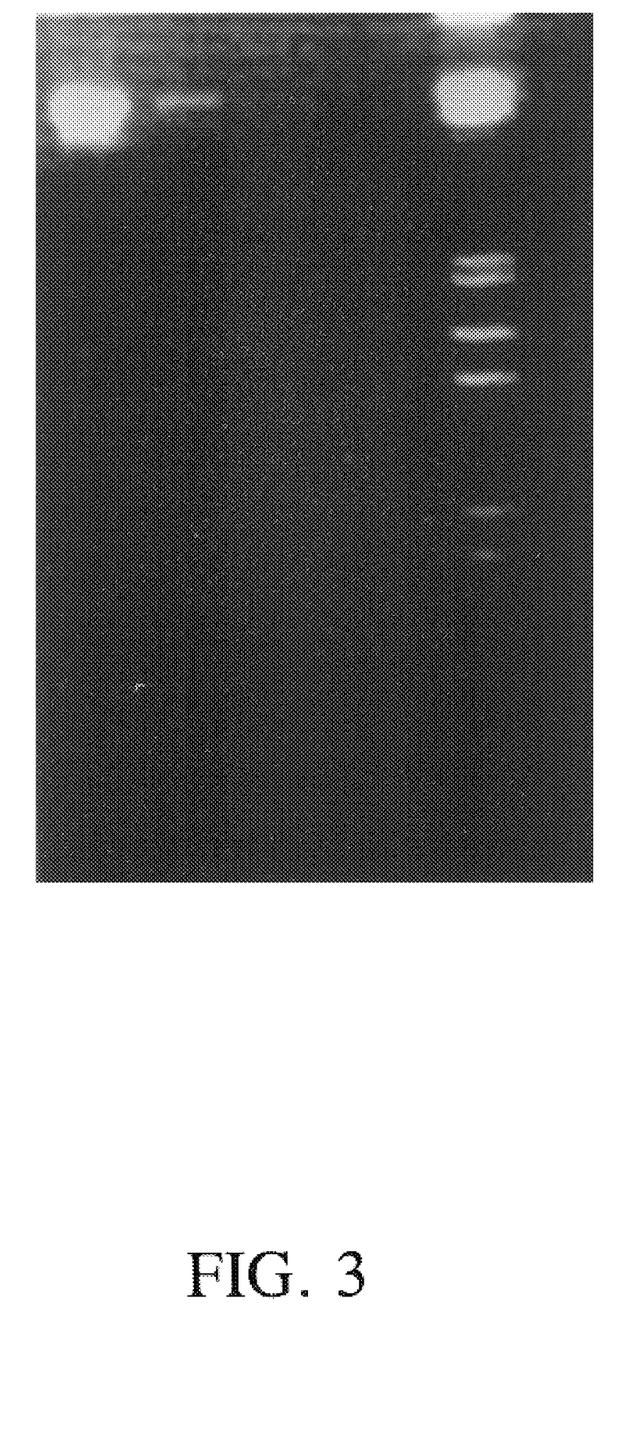
FIG. 3 shows electrophoretic separation of plasmid DNA target sequences prepared by the method of the subject invention.

Complementary primers SEQ ID NO 1,2,3 or 4 are used in the SSA method. The reaction contained about 50 mM KCl, about 10 mM Tris-HCl (pH 9), about 0.1% Triton X-100, about 0.2 mM each dNTP, about 2.0 mM MgCl$_2$, about 2 pmoles of one of the four primers listed below, and about 670 μg of ligated genomic DNA, all in a final volume of about 98 μl. The reaction mixture is covered with mineral oil and cycling was as follows: about 95° C., approximately 60 seconds, one cycle, template denaturation; about 95° C., approximately 60 seconds, about 50° C., approximately 120 seconds; and about 74° C., approximately 4 minutes for about 4 cycles. The reaction is then paused and approximately 2 pmoles of the complementary primer is added to the reactions. Cycling is then continued for about 21 cycles. The reaction set up is shown below in Table 1. Approximately 5 μl of each sample was loaded onto a 1.0% Agarose gel (Maniatis et al., Molecular Cloning, herein incorporated by reference) and electrophoresed at about 80 mA for approximately 120 minutes in TBE buffer. The results are shown in FIG. 2. HA is *Arabidopsis thaliana* cut with HAE III, HC is *Zea maize* cut with HAE III, TA is *Arabidopsis thaliana* cut with Taq I and TC is *Zea maize* cut with Taq I.

As seen in lanes 1–4 and 5–8, no distinct products or bands are visible. The smears that are evident are probably the result of DNA amplification since the size distribution of the smear is correlated with the presence or absence of a restriction site linker attached to the oligonucleotide. This procedure therefore can be optimized such that distinct banding patterns are observable, preferably between 200–100 bp in length, and in sufficient abundance for subcloning. The bands shown between lanes 4 and 5 are molecular markers, which are lambda DNA cut with EcoRI and HindIII.

Complementary primers used in this example are:

SEQ ID NO 1 5' GGAATTCACACACACACACACACA-CAC 3'
SEQ ID NO 2 5' GGAATTCGTGTGTGTGTGTGTGTGT-GTG 3'
SEQ ID NO 3 5' CACACACACACACACAC 3'
SEQ ID NO 4 5' GTGTGTGTGTGTGTGTGTG 3'

TABLE 1

| PCR RXN SETUP (100 μl reaction) | | | | | | | | |
|---|---|---|---|---|---|---|---|---|
| | 1 | 2 | 3 | 4 | 5 | 6 | 7 | 8 |
| Ligated genomic DNA: | | | | | | | | |
| HC | 10 | 10 | | | | | | |
| HA | | | 10 | 10 | | | | |
| TC | | | | | 10 | 10 | | |
| TA | | | | | | | 10 | 10 |
| Primer: | | | | | | | | |
| SEQ ID NO. 1 | 2 | | 2 | | 2 | | 2 | |
| SEQ ID NO. 2 | 2 | | 2 | | 2 | | 2 | |

TABLE 1-continued

PCR RXN SETUP (100 μl reaction)

|  | 1 | 2 | 3 | 4 | 5 | 6 | 7 | 8 |
|---|---|---|---|---|---|---|---|---|
| SEQ ID NO. 3 |  | .6 |  | .6 |  | .6 |  | .6 |
| SEQ ID NO. 4 |  | .5 |  | .5 |  | .5 |  | .5 |
| dNTP | 8 | 8 | 8 | 8 | 8 | 8 | 8 | 8 |
| 25 mM Mg | 8 | 8 | 8 | 8 | 8 | 8 | 8 | 8 |
| 10xBuff. | 10 | 10 | 10 | 10 | 10 | 10 | 10 | 10 |
| dH₂O | 58 | 61 | 58 | 61 | 58 | 61 | 58 | 61 |

SSA is demonstrated by using a pUC119 vector into which mutant preproricin cDNA from *Ricinus communis* was cloned for a total of 5.1 kb. Complementary primers WMC4 (SEQ ID No. 5) and WMC6 (SEQ ID No 6), previously designed to mutagenize this template at amino acid 225, were used for the SSA template production. The reaction contained about 50 mM KCl, about 10 mM Tris-HCl (approximately pH 9), about 0.1% Triton X-100, about 0.2 mM each dNTP, about 2.0 mM $MgCl_2$ and about 20 pmoles of each of primers SEQ ID No. 5 and SEQ ID No. 6, and template plasmid DNA at the following amounts: about 10 ng, about 100 pg, about 10 pg and no template; all in a final volume of about 50 μl. The reaction was begun by adding all components except SEQ ID No. 6, covering the reaction with mineral oil, and cycling as follows: approximately 95° C., approximately 30 seconds, one cycle for template denaturation; approximately 95° C., approximately 30 seconds; approximately 55° C., approximately 30 seconds; approximately 74° C., approximately 5 minutes, about 4 cycles. The reaction is then paused and approximately 20 pg of SEQ ID No. 6 is added to the reactions. Cycling is then continued for about an additional 24 cycles. Approximately 5 μl of each sample was loaded onto a gel of approximately 1.0% Agarose gel and electrophoresed at about 80 mA for about 45 minutes in TBE buffer. The results are shown in FIG. 3.

Product of the correct size is seen in the about 10 ng and about 100 pg template lanes. Reduction of template amount to about 10 pg produces no observable product at about 5.1 kb, but rather a smear is observed over the entire lane. The no template control produced no product. Molecular weight markers are EcoR1+HindIII cut lambda DNA.

Complementary primer sequences for this example are:

SEQ ID NO. 5 5' CCTCTCCATGGTGACCCAGC-CCAAATATGGTTACC 3'

SEQ ID NO. 6 5' GGTAACCATATTTGGGCTGGGTCAC-CTTGGAGAGG 3'

TABLE 2

The lanes on the gel (FIG. 3) were setup as follows:

| | Lane 1 (10 μg DNA) | Lane 2 (100 pg DNA) | Lane 3 (10 pg DNA) | Lane 4 (Control) |
|---|---|---|---|---|
| DNA | 5 μL | 2 μL | 2 μL | 0 μL |
| SEQ ID NO. 5 | 2 μL | 2 μL | 2 μL | 2 μL |
| SEQ ID NO. 6 | 2 μL | 2 μL | 2 μL | 2 μL |
| dNTP | 4 μL | 4 μL | 4 μL | 4 μL |
| 25 mMg | 4 μL | 4 μL | 4 μL | 4 μL |
| 10xBuff | 5 μL | 5 μL | 5 μL | 5 μL |
| dH20 | 28 μL | 31 μL | 31 μL | 35 μL |
| VP | 50 μL | 50 μL | 50 μL | 50 μL |

The foregoing detailed description is for the purpose of illustration. Others skilled in the art can apply the knowledge described to preparing any targeted DNA using the described method. Such detail is solely for that purpose and those skilled in the art can make variations therein without departing from the spirit and scope of the invention.

I claim:

1. A method for obtaining DNA of unknown sequence flanking a single site of known sequence comprising providing a circular DNA template containing DNA of unknown sequence flanking a target DNA of known sequence, annealing a first primer to said target DNA wherein said primer is complementary to the known sequence, extending said first primer using a DNA polymerase having strand displacement capability for at least a period of time to produce a linear DNA product containing said first primer sequence at at least two locations within the DNA product, producing a linear DNA product containing said first primer at the 5' end of said product and at least one first primer sequence 3' from said first primer at the 5' end of the linear DNA product.

2. The method of claim 1 further comprising adding a second primer wherein said second primer is complementary to said first primer to begin a polymerase chain reaction.

3. The method of claim 1 wherein said linear DNA is a marker.

4. The method of claim 3 wherein said marker is a simple sequence repeat.

* * * * *

SEQUENCE LISTING

<160> NUMBER OF SEQ ID NOS: 6

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: primer_bind
<222> LOCATION: (1)..(27)
<220> FEATURE:
<221> NAME/KEY: primer_bind
<222> LOCATION: (1)..(27)

<400> SEQUENCE: 1
ggaattcaca cacacacaca cacacac 27

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: primer_bind
<222> LOCATION: (1)..(28)
<220> FEATURE:
<221> NAME/KEY: primer_bind

```
<222> LOCATION: (1)..(28)

<400> SEQUENCE: 2
ggaattcgtg tgtgtgtgtg tgtgtgtg                                          28

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: primer_bind
<222> LOCATION: (1)..(19)
<220> FEATURE:
<221> NAME/KEY: primer_bind
<222> LOCATION: (1)..(19)

<400> SEQUENCE: 3
cacacacaca cacacacac                                                    19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: primer_bind
<222> LOCATION: (1)..(19)
<220> FEATURE:
<221> NAME/KEY: primer_bind
<222> LOCATION: (1)..(19)

<400> SEQUENCE: 4
gtgtgtgtgt gtgtgtgtg                                                    19

<210> SEQ ID NO 5
<211> LENGTH: 35
<212> TYPE: DNA
<213> ORGANISM: Artificial Sequence
<220> FEATURE:
<221> NAME/KEY: primer_bind
<222> LOCATION: ()
<223> OTHER INFORMATION: Description of Artificial Sequence: primer
<220> FEATURE:
<221> NAME/KEY: primer_bind
<222> LOCATION: (1)..(35)

<400> SEQUENCE: 5
ggtaaccata tttgggctgg gtcaccttgg agagg                                  35

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: primer_bind
<222> LOCATION: (1)..(35)
<220> FEATURE:
<221> NAME/KEY: primer_bind
<222> LOCATION: (1)..(35)

<400> SEQUENCE: 6
cctctccatg gtgacccagc ccaaatatgg ttacc                                  35
```